United States Patent
Allendorf et al.

(10) Patent No.: US 8,904,850 B1
(45) Date of Patent: Dec. 9, 2014

(54) MATERIALS, METHODS AND DEVICES TO DETECT AND QUANTIFY WATER VAPOR CONCENTRATIONS IN AN ATMOSPHERE

(75) Inventors: Mark D. Allendorf, Pleasanton, CA (US); Alex L. Robinson, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 368 days.

(21) Appl. No.: 13/253,274

(22) Filed: Oct. 5, 2011

Related U.S. Application Data

(60) Provisional application No. 61/390,781, filed on Oct. 7, 2010.

(51) Int. Cl.
*H01L 41/113* (2006.01)
*G01N 29/02* (2006.01)

(52) U.S. Cl.
USPC ............... 73/29.01; 310/313 B; 310/340

(58) Field of Classification Search
USPC ......... 73/29.01; 310/312, 313 B, 313 R, 322, 310/340
See application file for complete search history.

(56) References Cited

U.S. PATENT DOCUMENTS

| | | | | |
|---|---|---|---|---|
| 4,234,437 | A * | 11/1980 | Friberg et al. | 252/62.51 R |
| 5,323,636 | A | 6/1994 | McGowan et al. | |
| 5,571,944 | A | 11/1996 | Pfeifer et al. | |
| 6,031,315 | A * | 2/2000 | Abbott | 310/313 A |
| 6,257,048 | B1 * | 7/2001 | Hietala et al. | 73/24.01 |
| 6,491,740 | B1 * | 12/2002 | Wang et al. | 95/90 |
| 6,709,487 | B1 * | 3/2004 | Dong et al. | 95/117 |
| 7,134,319 | B2 * | 11/2006 | Liu | 73/31.06 |
| 7,815,716 | B2 * | 10/2010 | Mueller et al. | 95/90 |
| 8,440,012 | B2 * | 5/2013 | Hatcher et al. | 106/286.5 |
| 8,480,955 | B2 * | 7/2013 | Yaghi et al. | 422/68.1 |
| 8,718,956 | B2 * | 5/2014 | Hesketh et al. | 702/50 |
| 8,735,161 | B2 * | 5/2014 | Yaghi et al. | 436/43 |
| 2004/0023428 | A1 * | 2/2004 | Gole et al. | 438/48 |
| 2005/0193800 | A1 * | 9/2005 | DeBoer et al. | 73/1.06 |
| 2006/0014908 | A1 * | 1/2006 | Rotermund et al. | 525/452 |
| 2009/0060830 | A1 * | 3/2009 | Garcia-Bennet | 423/592.1 |
| 2009/0143595 | A1 * | 6/2009 | James et al. | 546/327 |
| 2010/0288014 | A1 * | 11/2010 | Yao et al. | 73/24.06 |
| 2011/0197657 | A1 * | 8/2011 | Gole | 73/31.05 |
| 2012/0028846 | A1 * | 2/2012 | Yaghi et al. | 506/39 |

OTHER PUBLICATIONS

Chui, Stephen S-Y., et al. "A chemically functionalizable nanoporous material [Cu3 (TMA) 2 (H2O) 3] n." Science 283.5405 (1999): 1148-1150.*

Varghese, Oomman K., et al. "Ammonia detection using nanoporous alumina resistive and surface acoustic wave sensors." Sensors and Actuators B: Chemical 94.1 (2003): 27-35.*

(Continued)

*Primary Examiner* — Lisa Caputo
*Assistant Examiner* — Punam Roy
(74) *Attorney, Agent, or Firm* — Dorsey & Whitney LLP

(57) ABSTRACT

We have demonstrated that a surface acoustic wave (SAW) sensor coated with a nanoporous framework material (NFM) film can perform ultrasensitive water vapor detection at concentrations in air from 0.05 to 12,000 ppmv at 1 atmosphere pressure. The method is extendable to other MEMS-based sensors, such as microcantilevers, or to quartz crystal microbalance sensors. We identify a specific NFM that provides high sensitivity and selectivity to water vapor. However, our approach is generalizable to detection of other species using NFM to provide sensitivity and selectivity.

16 Claims, 6 Drawing Sheets

(56) References Cited

OTHER PUBLICATIONS

Lee, Jin-Hwan, et al. Nanoporous framework materials interfaced with mechanical sensors for highly-sensitive chemical sensing. No. SAND2010-2151C. Sandia National Laboratories, 2010.*

Kubo, Masaru, Watcharop Chaikittisilp, and Tatsuya Okubo. "Oriented films of porous coordination polymer prepared by repeated in situ crystallization."Chemistry of Materials 20 No. 9 (2008): 2887-2889.*

Allendorf, Mark D., et al. "Stress-Induced Chemical Detection Using Flexible Metal—Organic Frameworks." Journal of the American Chemical Society130 No. 44 (2008): 14404-14405.*

Fischer, Roland A., et al. "Selective Growth and MOCVD Loading of Thin Films of Metal Organic Frameworks on Various Substrates." Meeting Abstracts. No. 36. The Electrochemical Society, 2007.*

Guerrero, Victor Varela, et al. "HKUST-1 membranes on porous supports using secondary growth." Journal of Materials Chemistry 20 No. 19 (2010): 3938-3943.*

Yoo, Yeonshick, and Hae-Kwon Jeong. "Rapid fabrication of metal organic framework thin films using microwave-induced thermal deposition." Chemical Communications 21 (2008): 2441-2443.*

Zacher, Denise, et al. "Deposition of microcrystalline [Cu3 (btc) 2] and [Zn2 (bdc) 2 (dabco)] at alumina and silica surfaces modified with patterned self assembled organic monolayers: evidence of surface selective and oriented growth." Journal of Materials Chemistry 17(27) (2007): 2785-2792.*

Ameloot, Rob, et al. "Patterned growth of metal-organic framework coatings by electrochemical synthesis." Chemistry of Materials 21 (13) (2009): 2580-2582.*

Liu, Yunyang, et al. "Synthesis of continuous MOF-5 membranes on porous α-alumina substrates." Microporous and Mesoporous Materials 118.1 (2009): 296-301.*

Gascon, Jorge, Sonia Aguado, and Freek Kapteijn. "Manufacture of dense coatings of $Cu_3(BTC)_2$ (HKUST-1) on α-alumina." Microporous and Mesoporous Materials 113.1 (2008): 132-138.*

Hoummady, Moussa, Andrew Campitelli, and Wojtek Wlodarski. "Acoustic wave sensors: design, sensing mechanisms and applications." Smart materials and structures 6.6 (1997): 647.*

Cheeke, J.D.N.; Tashtoush, N.; Eddy, N; "Surface Acoustic Wave Humidity Sensor Based on the Changes in the Viscoelastic Properties of a Polymer Film," IEEE Ultrasonics Symposium, 1996: pp. 449-452.

Vetelino, K.A.; Story, P.R.; Mileham, R.D.; Galipeau, D.W.; "Improved dew point measurements based on a SAW sensor," Senors and Actuators B, 1996, v.35-36: pp. 91-98.

Wang, Q.M.; Shen, D.; Bulow, M.;Lau, M.L.; Deng, S.; Fitch, F.R.; Lemcoff, N.O.; Semanscin, J.; "Metallo-organic molecular sieve for gas separation and purification," Microporous and Mesoporous Materials, 2002, v.55: pp. 217-230.

Shekhah, O.; Wang, H.; Kowarik, S.; Schreiber, F.; Paulus, M.; Tolan, M.; Sternemann, C.; Evers, F.; Zacher, D.; Fischer, R.A.; Wöll, C.; "Step-by-Step Route for the Synthesis of Metal-Organic Frameworks," Journal of the American Chemistry Society, 2007, v.129: pp. 15118-152119.

Biemmi, E.; Darga, A.; Stock, N.; Bein, T.; "Direct growth of $Cu_3(BTC)_2(H_2O)_3 \cdot xH_2O$ thin films on modified QCM-gold electrodes—Water sorption isotherms," Microporous and Mesoporous Materials, 2008, v.114: pp. 380-386.

Ameloot, R.; Stappers, L.; Fransaer, J.; Alaert, L.; Sels, B.F.; De Vos, D.E.; "Patterned Growth of Metal-Organic framework Coating by Electrochemical Synthesis," Chemistry of Materials Communication v.21: pp. 2580-2582, May 12, 2009.

Zacher, D.; Shekhah, O.; Wöll, C.; Fischer, R.A.; "Thin films of metal-organic frameworks," Chemistry Society Reviews, 2009, v.38: pp. 1418-1429.

* cited by examiner

MATERIALS, METHODS AND DEVICES TO DETECT AND QUANTIFY WATER VAPOR CONCENTRATIONS IN AN ATMOSPHERE

CROSS-REFERENCE TO RELATED APPLICATIONS

This Application claims benefit of prior application 61/390,781 filed Oct. 7, 2010, and entitled "Materials, Methods and Devices to Detect and Quantify Water Vapor Concentrations in an Atmosphere," herein incorporated by reference.

STATEMENT OF GOVERNMENT INTEREST

The United States Government has rights in this invention pursuant to Contract No. DE-AC04-94AL85000 between the United States Department of Energy and Sandia Corporation, for the operation of the Sandia National Laboratories.

BACKGROUND

Field of the Invention

The invention relates to devices and methods for reliably measuring very low levels of water vapor in a surrounding atmosphere.

More specifically, the invention relates to nanoporous framework materials (NFM) which comprise a class of hybrid inorganic-organic crystalline materials whose pore structure and chemical properties can be rationally tailored by the selection of their component chemical moieties. Distinguishing features of NFM are rigid organic "linker" groups connected to either metal cations or covalently bound to main-group elements such as silicon and boron. These self-organize into two- and three-dimensional open-pore structures that can have extremely high surface areas. These structures retain their porosity upon removal of "guest" molecules (solvent or other), enabling them to serve as reversible sorbents for a variety of molecular species. NFM crystal structures also exhibit a degree of structural flexibility not found in other nanoporous materials, including zeolites, aerogels, synthetic opals, and nanotubes (both carbon- and non-carbon based).

Upon absorption of molecules from either the gas phase or solution, many NFM undergo reversible changes in the dimensions of their unit cells. These properties suggest several routes to humidity sensing in which the transduction mechanisms are:

1.) the stress induced at an interface between a flexible NFM layer and a static microcantilever ($\mu$CL) equipped with a built-in piezoresistive stress sensor;

2.) a change in the resonant frequency of an oscillating microcantilever induced by water adsorption; and 3.) a change in the resonant frequency of a surface acoustic wave (SAW) device, quartz crystal microbalance (QCM), or other resonating mechanical sensor upon water adsorption.

We have demonstrated the feasibility of all three concepts using devices we fabricated, showing that easily measured signals can be generated through adsorption-induced stress or frequency changes caused by uptake of vapor-phase water in NFM layers coated on the above mentioned sensor substrates.

NFM coatings on sensors possess a number of features that make them potentially superior to polymers and other coatings currently used to impart sensitivity and selectivity to chemical sensors. Firstly, large stress-induced signals are observed upon analyte adsorption due to the large changes in lattice dimensions that can be achieved. Secondly, some NFM have been observed to possess surface areas of up to 6000 $m^2/g$: a result approximately six times greater than a zeolite. This makes these materials potentially highly effective sorbents that would increase sensitivity in sensors detecting either mass or stress changes. Third, the ability to tailor NFM pore sizes by changing the chemical nature of the linking molecule; changing the metal center; or changing the pore geometry, enables both the chemical selectivity and adsorption properties to be optimized in a rational way. Fourth, effective mechanical linkages between NFM crystals and a substrate can be created by covalent bonding schemes that anchor the crystal to the sensor surface. These qualities result in robust, stable sensors capable of generating large signals from small quantities of targeted analytes.

BRIEF DESCRIPTION OF THE DRAWINGS

The accompanying drawings, which are hereby incorporated into the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF ONE OR MORE EMBODIMENTS

We have demonstrated that SAW devices coated with a NFM film can perform ultrasensitive water vapor detection. In particular, we have shown that a metal-organic framework (MOF) and a subclass of a NFM, was used as the nanoporous coating material. CuBTC, also known as HKUST-1, is shorthand nomenclature for copper (II) benzene-1,3,5-tricarboxylate [chemical formula $Cu_3(BTC)_2(H_2O)_3$]. Other NFMs, e.g., NOTT-100 (biphenyl-3,3',5,5'-tetracarboxylic acid) and NOTT-101 (terphenyl-3,3',5,5'-tetracarboxylic acid) may be similarly useful but CuBTC is particularly advantageous because it has been shown to be capable of absorbing as much as 40% water by weight (Q. M. Wang et al. *Microporous and Mesoporous Materials*, 2002, v. 55 (2): pp. 217-230.). We note that Biemmi et al. (Biemmi et al, *Microporous and Mesoporous Materials*, 2008, v. 114 (1-3): pp. 380-386, herein incorporated by reference) speculated that CuBTC could be used in humidity sensing applications and measured water vapor adsorption isotherms by coating the gold electrodes of a QCM using a thiol-based self-assembled monolayer (SAM) to attach the MOF onto the gold electrodes. Although this method was sufficient to detect high water vapor concentrations (low sensitivity), they found that the device had to be heated to 70° C. to achieve full reversibility. However, the time required to fully desorb the water at this elevated temperature was still four hours, severely limiting its use as a practical sensor. In addition, this temperature is at the upper limit of the SAM (self-assembled monolayer) thermal stability and is likely to limit the durability of their device. Ameloot et al (Ameloot et al., *Chemistry of Materials*, 2009, v. 21(13): pp. 2580-2582, herein incorporated by reference) demonstrated moisture sensing with a CuBTC coated QCM down to 6.6% RH (1842 ppmv) with an estimated limit of detection of 30 ppmv water.

Through the use of much more sensitive sensor substrates, we have demonstrated an improvement of this capability by nearly 3 orders of magnitude demonstrating the detection of water vapor at concentrations in nitrogen from less than about 0.05 ppmv to over 12,000 ppmv relative to 1 atmosphere pressure (see TABLE 1 below).

TABLE 1

| Frost Point (° C.) | PPM(V) | % RH |
|---|---|---|
| −95.0 | 0.038 | 0.0001 |
| −80.0 | 0.54 | 0.002 |
| −70.0 | 2.59 | 0.011 |
| −60.0 | 10.73 | 0.046 |
| −50.0 | 39.05 | 0.168 |
| −40.0 | 127 | 0.549 |
| −30.0 | 377 | 1.625 |
| −20.0 | 1024 | 4.413 |
| −10.0 | 2582 | 11.11 |
| 0.0 | 6092 | 26.123 |
| 10.0 | 12318 | 52.492 |

Equivalent expressions of water vapor.

Figure 1A:
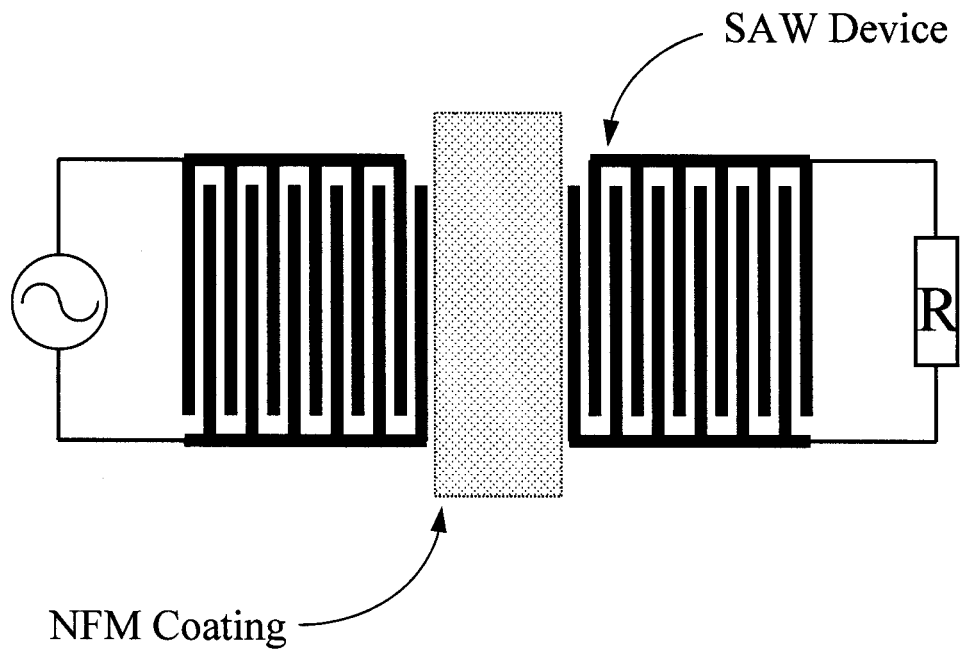
FIG. 1A shows a schematic of one embodiment of the device disclosed herein with an NFM coating disposed between the interdigitated electrodes of the SAW.
Figure 1B:
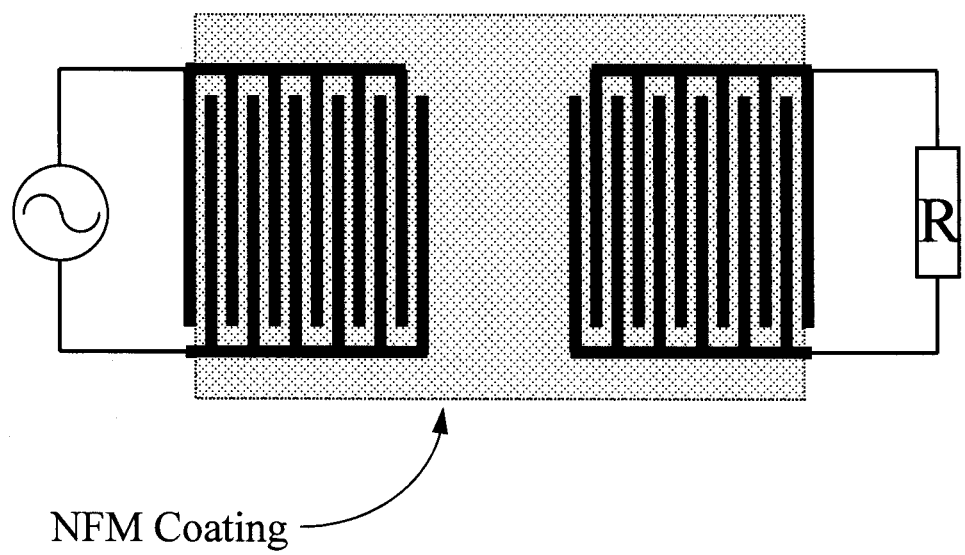
FIG. 1B shows a schematic of a second embodiment with the NFM coating covering both of the interdigitated electrodes of the SAW device disclosed herein as well as the space between the electrodes.

In our demonstration, the CuBTC coating was grown directly on the silicon oxide surface of the quartz SAW device. The film was deposited using the solution-based methods of Fischer et al. (D. Zacher et al. *Chemical Society Reviews*, 2009, v. 38(5): pp. 1418-1429, herein incorporated by reference), that is, for the case of HKUST-1, the two components, anhydrous copper(II)acetate [$Cu(CH_3CO_2)_2$ or $CuAc_2$] and 1,3,5-benzenetricarboxylic acid [$C_9H_6O_6$ or $H_3BTC$], were separately dissolved in ethanol having a trace amount of dimethylformamide (DFM): $Cu(CH_3CO_2)_2$ to a concentration of 1 mM-10 mM and $H_3BTC$ at a concentration of between 0.1 mM-1 mM. These solutions were held at a temperature of between 20° C. and 63° C. and the substrate immersed into each solution in a cyclic manner for about 30 minutes. Each step was followed by a thorough rinsing in pure ethanol. The deposited MOF layers are found to grow with the [100]direction perpendicular to the surface. Moreover, the resulting covalent bonds established across the exposed silica surface of the SAW eliminated the need for the use of a SAM layer entirely if the coating is deposited between the SAW interdigitated electrodes as shown in FIG. 1A, producing a durable, thermally stable coating that can be heated up to 250° C. to rapidly and efficiently remove the adsorbed water. The coating may also be deposited over most of the SAW surface such as shown in FIG. 1B but because the surface of the electrodes did not provide a compatible bonding surface without a SAM layer it was found that some delamination resulted between the NFM coating these surfaces.

Figures 2A, 2B, 2C:
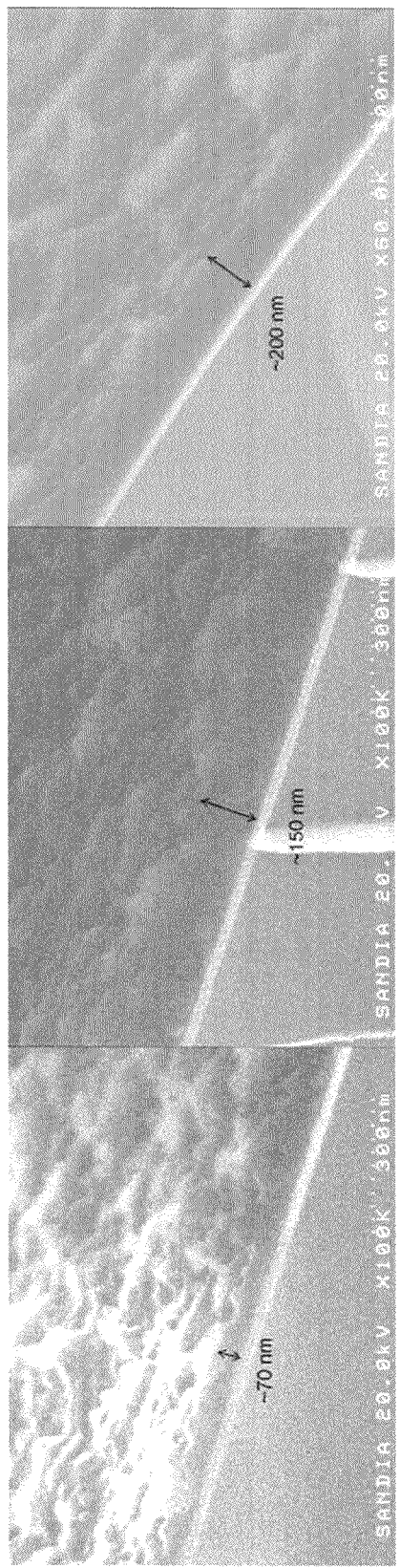
FIG. 2A show a scanning electron microscope (SEM) image of copper (II) benzene-1,3,5-tricarboxylate having the chemical formula $Cu_3(BTC)_2(H_2O)_3$ (hereinafter identified as CuBTC) grown on a silicon oxide surface using the Okubo method described herein after 20 cycles.
FIG. 2B shows the thickness of the CuBTC grown on the silicon oxide surface as described after 40 cycles.
FIG. 2C shows the thickness of the CuBTC grown on the silicon oxide surface as described after 60 cycles.
Figure 3:
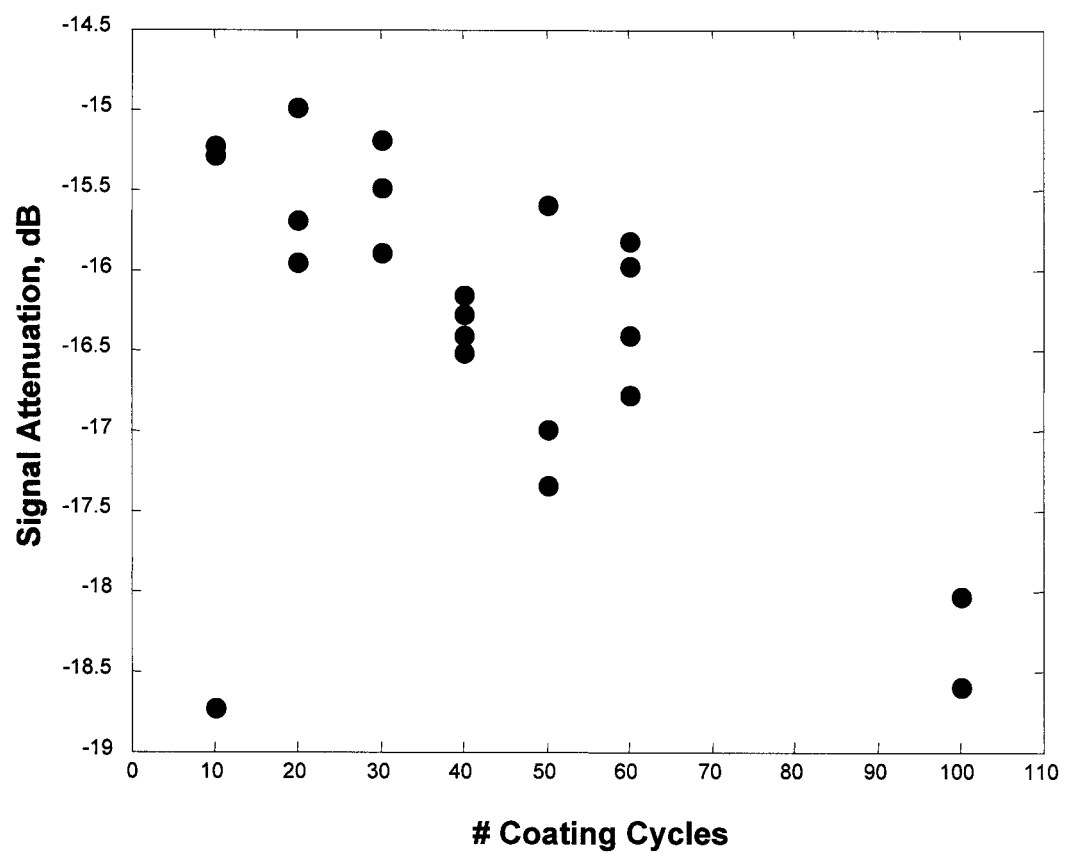
FIG. 3 shows the sensitivity response of the SAW device disclosed herein as the thickness of the CuBTC coating increases.

The coatings that result from this process are polycrystalline and uniform, continuous films with thicknesses proportional to the number of cyclical deposition cycles (see FIGS. 2A-2C). The crystallites forming the coating layer are on the order of 100-150 nm in diameter. The designed thickness of the coating can range from below 50 nm to over 1 micron, with the practical thickness limited by viscoelastic coupling of the acoustic energy into the sensing layer in the case of a SAW or QCM, or by mass-induced attenuation of the mechanical motion in the case of a microcantilever. For a SAW the effective thicknesses of these films appears to be limited to about 200 nm (~60 cycles), as can be seen in FIG. 3, after which the sensitivity of the device no longer increases with increasing coating thickness.

Figure 4:
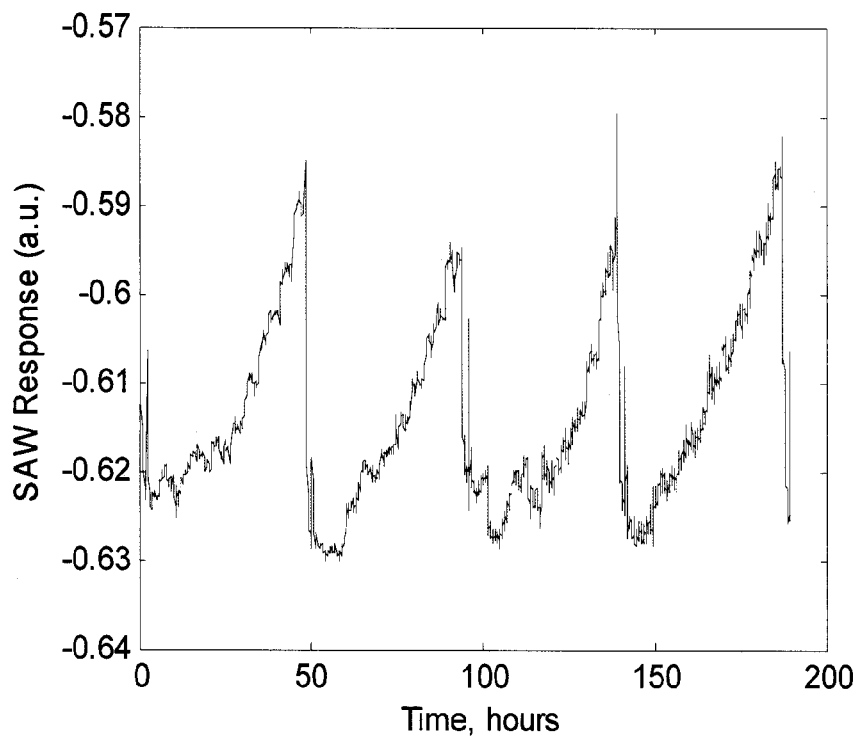
FIG. 4 shows the water vapor response of a SAW device coated with a CuBTC layer.
Figure 5:
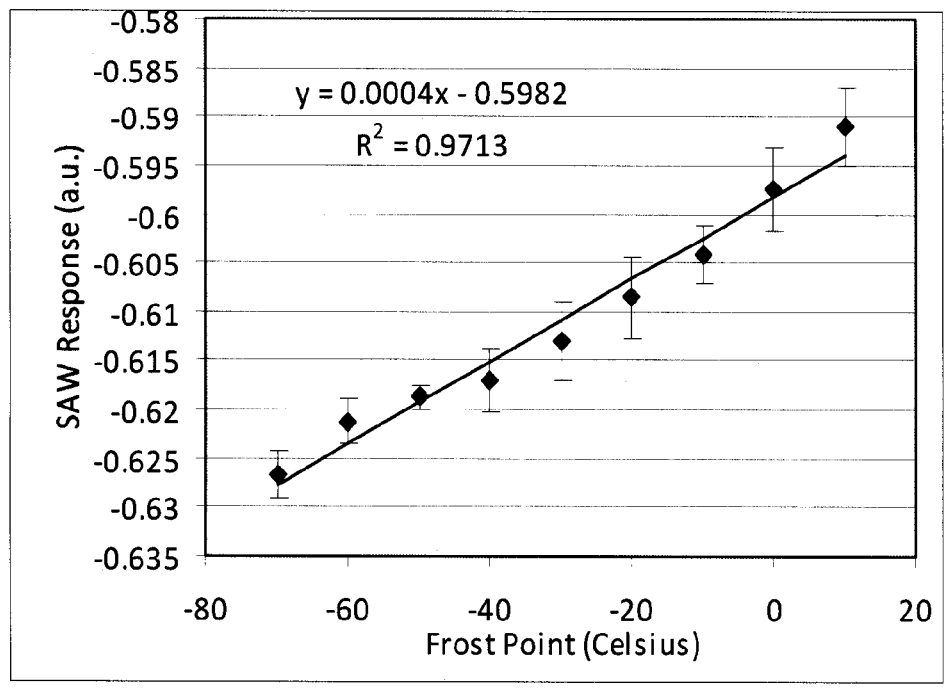
FIG. 5 shows a summary of the data provided in FIG. 3 showing average and standard deviation after stabilization at each moisture level.
Figure 6:
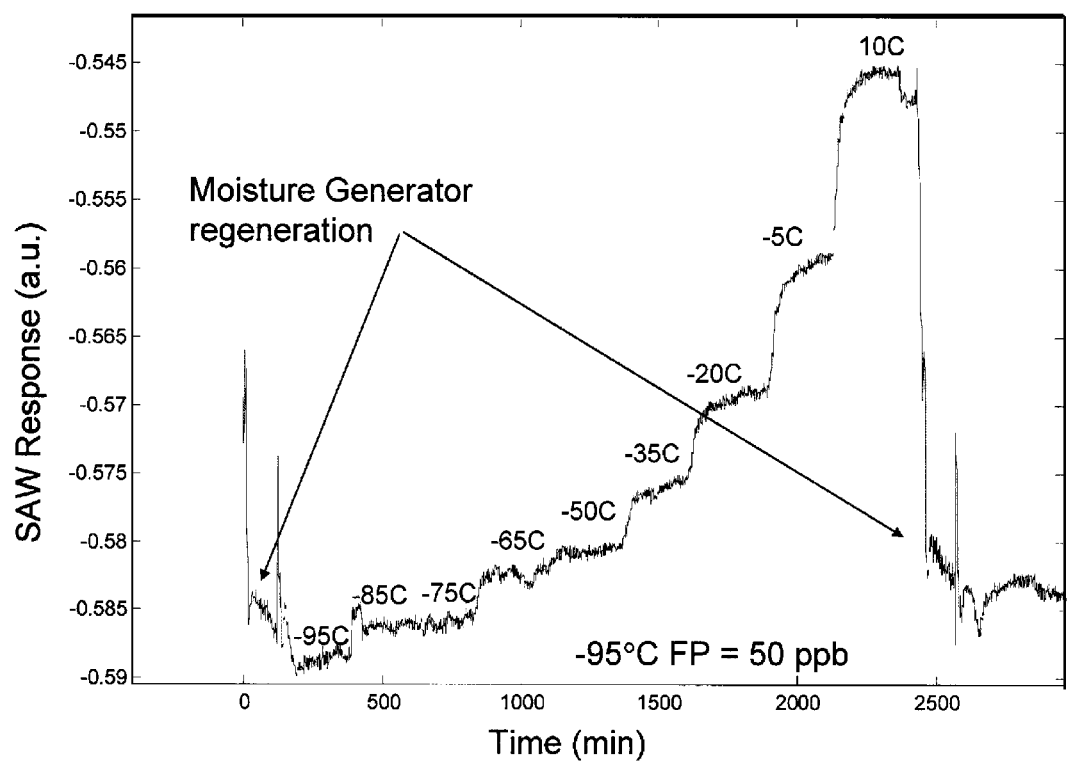
FIG. 6 shows the response of a CuBTC-coated SAW exposed to very low moisture levels.

The device described herein was tested by placing the coated SAW sensor in a sealed, confined space and creating a controlled atmosphere using a humidity generator (Model 3900 obtained from the Thunder Scientific Corporation, Albuquerque, N. Mex.) capable of providing a known humidity value traceable to NIST standards. FIG. 4 shows four cycles of data for a CuBTC-coated SAW device as described herein. While the ambient room temperature was stable at 20° C., the SAW fixture temperature was slightly elevated at 27° C. due to self-heating of the continuously operating SAW. Significant time is allowed for the humidity generator to achieve precise stability (+/−0.1° C. Frost Point) at each setting and for the plumbing to equilibrate. However, the CuBTC-coated SAW sensor response was found to be much faster, precisely tracking the in-line chilled mirror reference sensor when the flow rate and dead volume of the vapor generation system between the reference sensor and the downstream SAW are accounted for. The data is summarized in FIG. 5, showing an average standard deviation of +/−7° C. frost point. As seen in FIG. 6, the device is able to respond to humidity levels as low as −95° C. (0.050 ppm $H_2O$ at standard temperature and pressure). This concentration is approximately 600 times lower than the estimated limit of detection reported by the prior art.

Figure 7A:
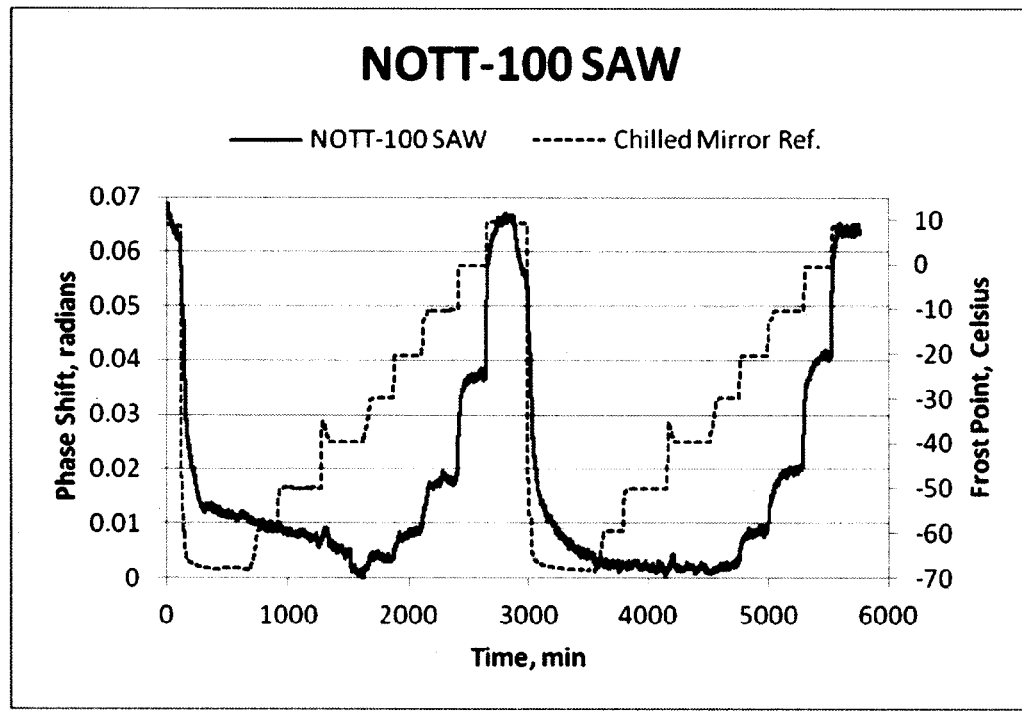
FIGS. 7A and 7B show the response of a SAW device coated with NOTT-100 and NOTT-101, respectively, and exposed to the same very low moisture levels to which the CuBTC-coated SAW device was exposed.
Figure 7B:
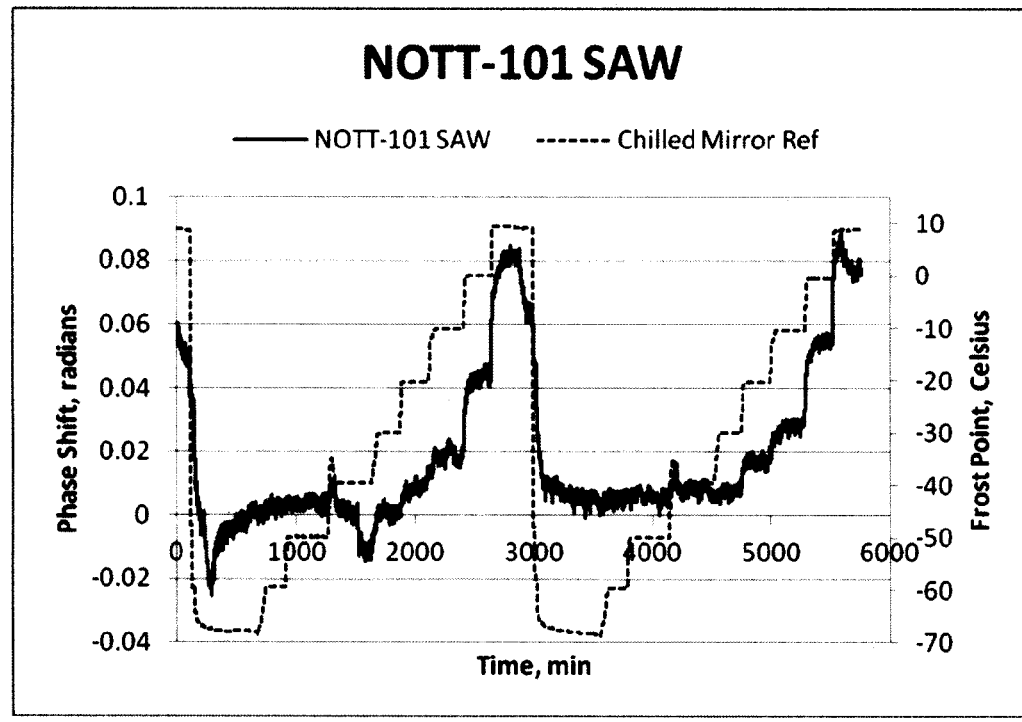

Finally, it is believed that these devices, employing coatings analogous to HKUST-1, are capable of similar behavior. In particular, and as noted above, materials such as the isostructural MOF polymers of composition [$Cu_2(L)(H_2O)_2$] (where L is a tetracarboxylate ligand), also known as NOTT-nnn may be useful as sensor materials. As demonstrated by initial results with NOTT-100 and NOTT-101 shown in FIGS. 7A and 7B, respectively, it is apparent that an effect similar to that demonstrated by NKUST-1 is provided. Those skilled in the art would, therefore, anticipate that these and many other similar materials would behave in the same manner.

The combination of these results shows that a practical sensor capable of detecting water vapor down to a frost point of −95° C. (0.050 ppm $H_2O$ at standard temperature and pressure) is feasible. This is the lowest water vapor concentration that can be reliably generated by a commercial instrument.

From the foregoing it will be appreciated that, although specific embodiments of the invention have been described herein for purposes of illustration, various modifications and other alternatives or adaptations may be made without deviating from the spirit and scope of the invention. Accordingly, the present invention is not limited to the specific embodiments as illustrated herein, but is only limited by the following claims.

Lastly, to the extent necessary to understand or complete the disclosure of the present invention, all publications, patents, and patent applications mentioned herein are expressly incorporated by reference therein to the same extent as though each were individually so incorporated.

What is claimed is:

1. A humidity sensor comprising;
a surface acoustic wave (SAW) device formed on one surface of a quartz substrate, the SAW device comprising a plurality of interdigitated electrodes; and
a material comprising a nanoporous framework material (NFM) coating, wherein the NFM coating is covalently bonded to at least a portion of the one surface between the plurality of interdigitated electrodes,
wherein the NFM coating is selected from the list consisting of copper (II) benzene-1,3,5-tricarboxylate, copper (II) biphenyl-3,3',5,5'-tetracarboxylic acid, and copper (II) terphenyl-3,3',5,5'-tetracarboxylic acid.

2. The sensor of claim 1, wherein the NFM coating has a thickness of between about 50 nm to about 200 nm.

3. The sensor of claim 1, wherein the NFM coating is comprised of copper (II) biphenyl-3,3',5,5'-tetracarboxylic acid.

4. The sensor of claim 1, wherein the NFM coating is comprised of copper (II) benzene-1,3,5-tricarboxylate.

5. The sensor of claim 1, wherein the NFM coating is bonded to at least a portion of a silicon oxide surface of the SAW device.

6. The sensor of claim 1, wherein the NFM coating is bonded over a substantial portion of a surface of the SAW device.

7. The sensor of claim 1, wherein a first interdigitated electrode is disposed near one end of the quartz substrate and a second interdigitated electrode is disposed near an opposite end of the quartz substrate.

8. A humidity sensor comprising;
a surface acoustic wave (SAW) device formed on one surface of a quartz substrate, the SAW device comprising a plurality of interdigitated electrodes; and
a material comprising a nanoporous framework material (NFM) coating, wherein the NFM coating is covalently bonded to at least a portion of the one surface between the plurality of interdigitated electrodes,
wherein the sensor is configured to detect water vapor in an ambient atmosphere having a concentration of less than about 0.05 ppmv to at least 12,000 ppmv.

9. The sensor of claim 8, wherein the NFM coating has a thickness of between about 50 nm to about 200 nm.

10. The sensor of claim 8, wherein the NFM coating is selected from the list consisting of copper (II) benzene-1,3,5-tricarboxylate, copper (II) biphenyl-3,3',5,5'-tetracarboxylic acid, and copper (II) terphenyl-3,3',5,5'-tetracarboxylic acid.

11. The sensor of claim 8, wherein the NFM coating is comprised of copper (II) benzene-1,3,5-tricarboxylate.

12. The sensor of claim 8, wherein the NFM coating is bonded to at least a portion of a silicon oxide surface of the SAW device.

13. The sensor of claim 8, wherein the NFM coating is bonded over a substantial portion of a surface of the SAW device.

14. The sensor of claim 8, wherein the NFM coating is covalently bonded to a surface of the quartz substrate without a self-assembled monolayer.

15. The sensor of claim 8, wherein a first interdigitated electrode is disposed near one end of the quartz substrate and a second interdigitated electrode is disposed near an opposite end of the quartz substrate.

16. A humidity sensor comprising;
a surface acoustic wave (SAW) device formed on one surface of a quartz substrate, the SAW device comprising a plurality of interdigitated electrodes; and
a material comprising a nanoporous framework material (NFM) coating, wherein the NFM coating is covalently bonded to at least a portion of the one surface between the plurality of interdigitated electrodes,
wherein the NFM coating is covalently bonded to a surface of the quartz substrate without a self-assembled monolayer.

* * * * *